United States Patent [19]

Bach et al.

[11] Patent Number: 4,730,922

[45] Date of Patent: Mar. 15, 1988

[54] ABSORBANCE, TURBIDIMETRIC, FLUORESCENCE AND NEPHELOMETRIC PHOTOMETER

[75] Inventors: David T. Bach, Wilmington; Charles W. Robertson, Jr., Rockland, both of Del.

[73] Assignee: E. I. Du Pont de Nemours and Company, Wilmington, Del.

[21] Appl. No.: 731,781

[22] Filed: May 8, 1985

[51] Int. Cl.⁴ .................... G01N 21/49; G01N 21/59; G01N 21/64

[52] U.S. Cl. ..................... 356/73; 356/317; 356/328; 250/458.1

[58] Field of Search ............ 356/73, 326, 328, 317, 356/318, 244, 246; 250/365, 458.1, 459.1, 461.1, 461.2

[56] References Cited

U.S. PATENT DOCUMENTS

| | | | |
|---|---|---|---|
| 2,381,414 | 8/1945 | Wilkie | 250/365 |
| 2,827,825 | 3/1958 | White | 356/301 |
| 2,971,429 | 2/1961 | Howerton | 250/365 |
| 3,518,009 | 6/1970 | Shamos et al. | 356/246 |
| 3,702,736 | 11/1972 | Coggeshall | 356/328 |
| 3,972,627 | 8/1976 | Rabl et al. | 356/246 |
| 4,012,147 | 3/1977 | Walrafen | 356/326 |
| 4,060,327 | 11/1977 | Jacobowitz et al. | 356/328 |
| 4,074,939 | 2/1978 | Rabl | 250/574 |
| 4,305,660 | 12/1981 | Kallet | 356/73 |
| 4,426,154 | 1/1984 | Steen | 356/73 |
| 4,440,497 | 4/1984 | Carey et al. | 356/318 |

FOREIGN PATENT DOCUMENTS

| | | | |
|---|---|---|---|
| 116289 | 9/1979 | Japan | 356/246 |
| 0042116 | 4/1981 | Japan | 356/73 |
| 56124 | 3/1984 | Japan | 356/319 |
| 78334 | 5/1985 | Japan | 356/246 |

OTHER PUBLICATIONS

Walfren, *Applied Spectroscopy*, vol. 29, No. 2, 1975, pp. 179–185.

Walfren, *Applied Spectroscopy*, vol. 31, No. 4, Jul./Aug. 1977, pp. 295–298.

*Primary Examiner*—F. L. Evans

[57] ABSTRACT

An absorbance, turbidimetric, fluorescence, and nephelometric photometer is constructed by providing a sample cell having a rectangular absorbance/turbidimetric cross-section for radiation. The cells exit aperture is positioned to be the entrance aperture for a grating which separates the light according to wavelength and impingement on an array detector.

10 Claims, 17 Drawing Figures

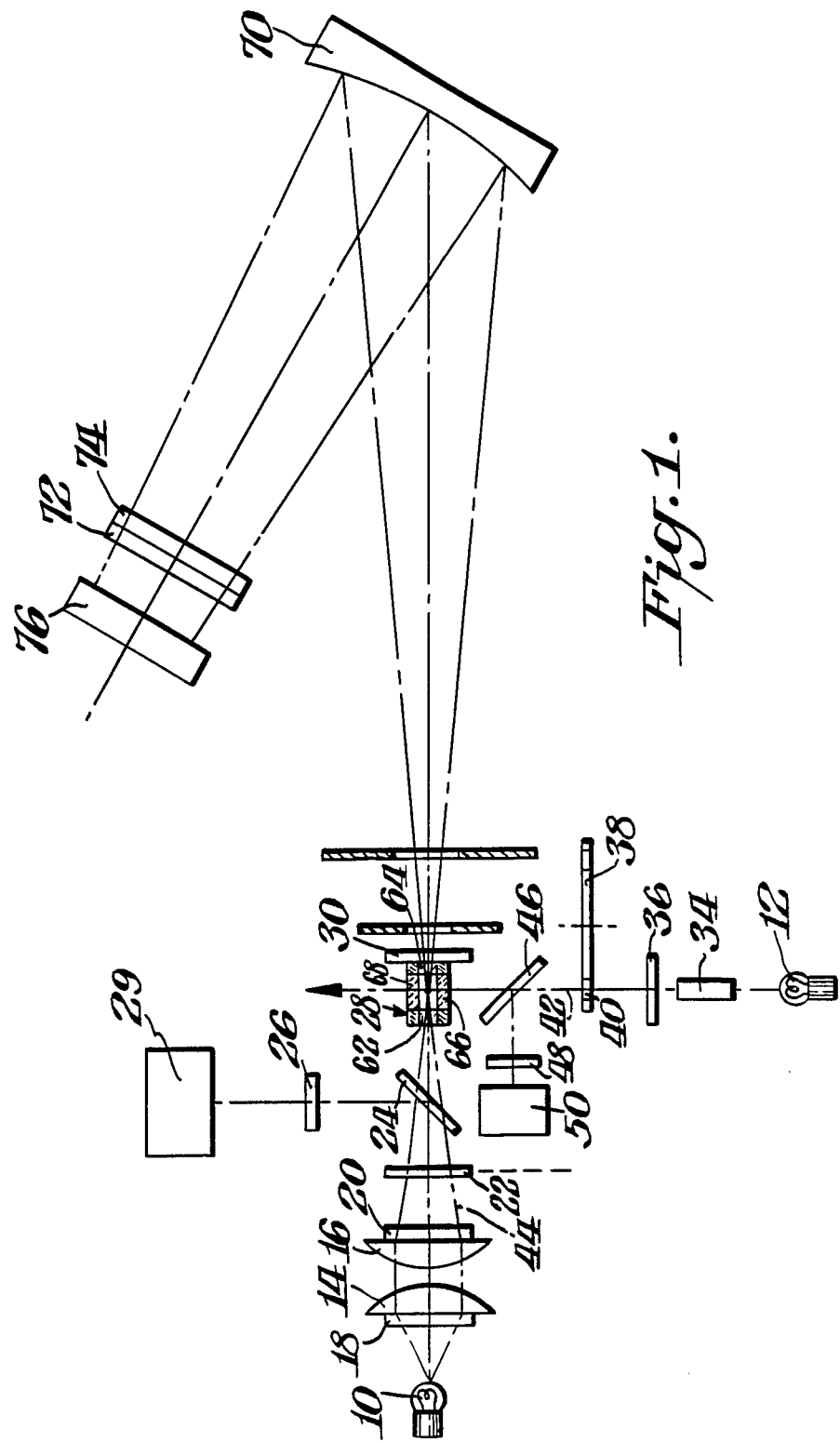

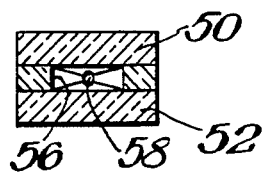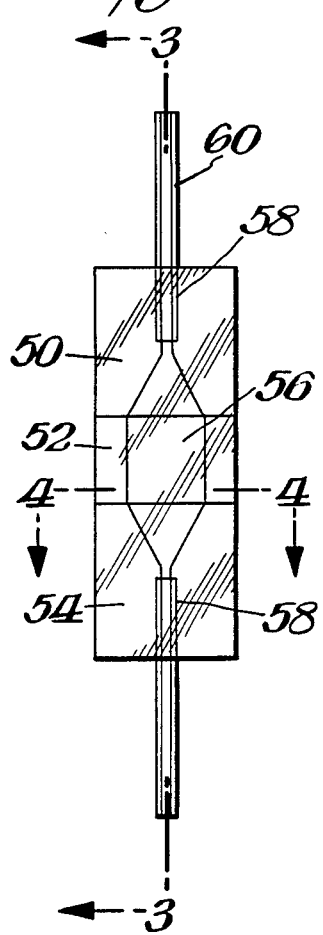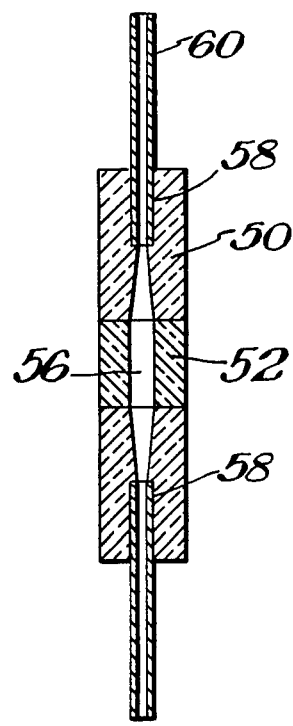

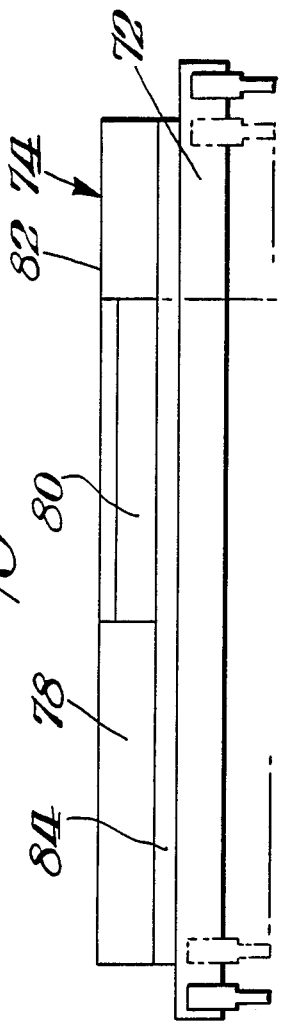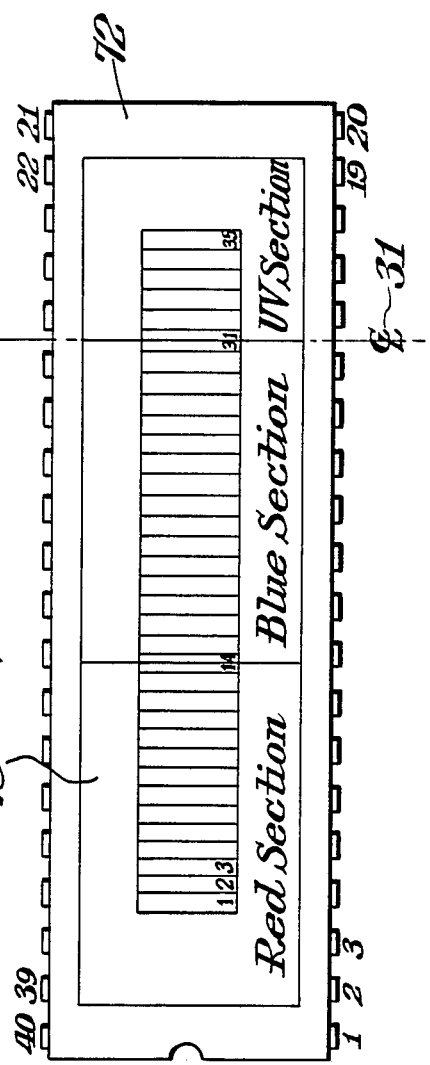

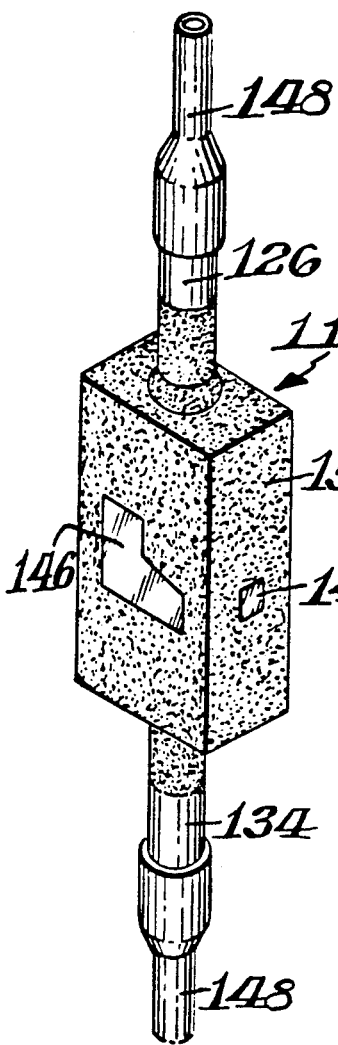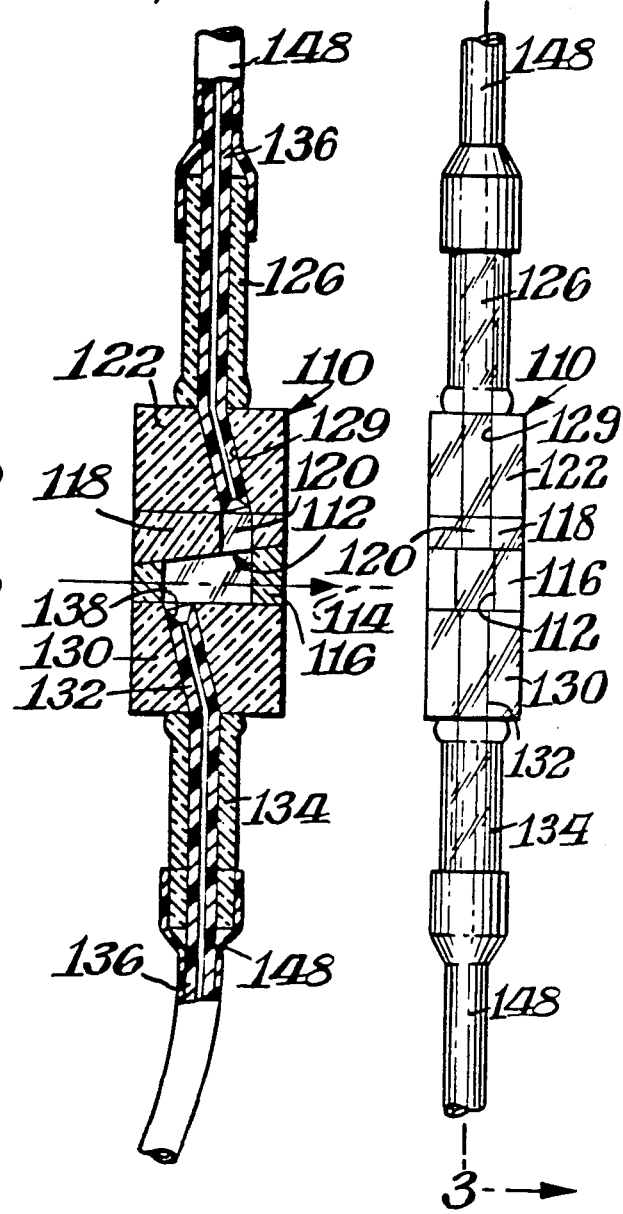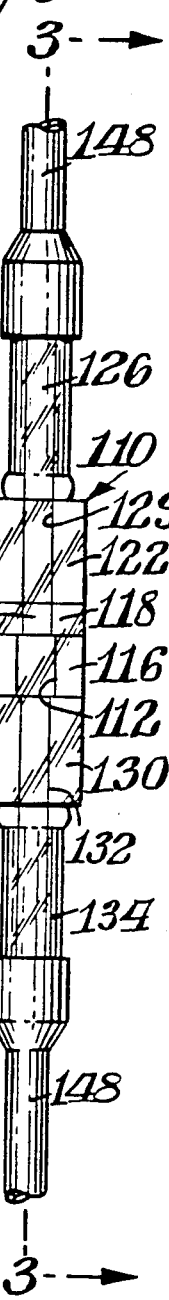

ABSORBANCE, TURBIDIMETRIC, FLUORESCENCE AND NEPHELOMETRIC PHOTOMETER

BACKGROUND OF THE INVENTION

Many of the analytical and diagnostic tests currently being performed require the use of a photometer to measure light or radiation being absorbed, scattered or emitted from a sample cell. The analyte to be measured or tested is either deposited in a discrete sample cell, cuvette, or passed through a sample cell of the flow type in which a continuous flow of liquid to be analyzed is passed. The physical properties of the sample that are typically measured are the absorbance of light passing through the cell, the reduction of light passing through the cell due to scatter caused by particles within the cell, the ninety degree light scattered from a source by particles within a cell (nephelometric) or finally the materials within the cell that fluoresce when excited by a proper exciting radiation.

Various photometers have been developed to measure one or sometimes two of the above noted physical properties. This typically necessitates the use of several photometers in order to perform all of these measurements. With the increasing number of analytical and diagnostic tests now available this need of measuring all of the above properties of a sample analyte has become more of a necessity than previously. This has increased significantly the cost of performing such analysis and has created the need for a low cost photometer capable of performing all of these four functions.

It is also required that the various measurements of the physical properties of the analyte in a sample cell be made with a high degree of sensitivity. In addition it is desirable to be able to subject the analyte to a single wavelength of light, to multiwavelengths of light for some of the more difficult chemistries used in an analysis as well as to make bichromatic wavelength measurements. An additional factor which must be considered is that of straylight rejection. This is particularly true when the fluorescent light emitted by the sample is to be measured. Typically, fluorescent light emitted is of a low intensity and hence much more subject to interference by straylight, particularly by the straylight from the exciting radiation which creates the fluorescence in the first place. Most of these factors may be summarized under the name of detection flexibility i.e., the photometer must have a high degree of flexibility and be able to detect various wavelengths of light.

While there have been many photometers developed in the prior art most of these are not able to measure all oft he four physical criteria set forth above. For example, U.S. Pat. No. 4,060,327 issued Nov. 29, 1977 to International Business Machines Corporation passes light, admitted through an entrance slit, through a sample cell and thence to a pair of gratings which disperse the light admitted through the slit into two separate dispersed beams. The separate beams are then focused on linear arrays of photodiodes providing outputs proportional to the intensity of the light rays at the different wavelengths received thereby. While this system operates across a relatively wide band of radiant energy it is capable only of absorbance and turbidimetric measurements.

Another photometer system is described in U.S. Pat. No. 4,426,154 issued Jan. 17, 1984 to Wetzlar. Wetzlar describes a photometer for measuring fluorescent light, scattered light and/or absorbed light; it cannot measure nephelometric light. Furthermore, the system does not appear to have an effective means of removing straylight from that impinging upon the various photodetectors. Baker Instruments has just announced the introduction of a chemistry system featuring optics enabling it to operate in both absorbance and fluorescence modes. It uses a 180° optical system, apparently like Wetzlar, and is said to include discrete excitation and emission filters. The discrete filters reduce the straylight effects that often occur in a monochrometer. It does not appear capable of nephelometric measurement.

It should be noted that these prior art patents which are typical of all the prior art are limited in sensitivity, versatility and tend to be relatively costly in requiring plural photometers in order to measure all four physical parameters of an analyte, i.e. absorbance, turbidimetry, fluorescence and nephelometry.

SUMMARY OF THE INVENTION

To overcome many of the deficiencies of the prior art and to provide a low cost unit which is able to measure the absorbance, turbidity, fluorescence and nephelometric properties of a liquid sample, this invention provides a sample cell which is an integral part of the grating aperture provided for an array detector. The sample cell has a square absorbance/ turbidimetric cross-section for the radiation passing therethrough. Two different light sources are positioned for passing radiation through the cell; one is positioned for passing light directly through the cell to the grating; the other is positioned for passing light through the cell at a ninety degree angle to the first mentioned light source to permit fluorescence and nephelometric measurements. In both cases however, the sample cell has the special cross-sections for the radiation and positions a wavelength filter between the cell and the grating. The system of this type has a high degree of flexibility in that it can make both single and bichromatic wavelength measurements. It can also make multiwavelength analyses for some of the more difficult chemistries present in the sample cell. To enhance fluorescence measurements a straylight filter section is used between the grating and array.

This invention finds use in a multifunction photometer having a sample cell in which a liquid is interrogated, a holographic grating, an array of photodiodes, and a first source of radiation directed along a first axis through the cell to the grating for dispensing the radiation according to wavelength onto respective photodiodes, thereby to provide signals corresponding to the intensity of the radiation at each detector wavelength region. This photometer is improved in accordance with this invention by forming the sample cell to define an exit aperture having a rectangular cross-section perpendicular to the axis, which aperture is positioned to be the entrance aperture for the grating. In this manner a light emitted from the sample cell, whether it be absorbed light, scattered light, fluorescent light or nephelometric light, is all directed through the exit aperture to the grating for separation according to wavelength and impingement upon an array detector so that the intensities of the radiation at the corresponding wavelengths may be independently measured.

The sample cell has a rectangular cross-section perpendicular to the first axis that is larger in all dimensions than the exit aperture cross-section. A second source of radiation is directed along a second axis perpendicular to the first axis for exciting fluorescence in liquid samples in the sample cell, the sample cell having a fluorescent entrance (and exit if desired) aperture lying on the second axis, the fluorescent radiation exiting through the grating entrance aperture. Finally, the cross-sectional areas of the fluorescence entrance (and exit) apertures are each greater than the cross-sectional area of the grating entrance aperture. A straylight filter is disposed between the grating and the photodiode array, the filter having two filter section lines for excitation and emission cut points selected to match fluorophores used in the liquid sample. Means are provided for scanning the several output signals from the diode array to obtain a wavelength distribution of radiation intensities emitted from the sample cell.

The photometer thus produced is a highly versatile, low cost unit having the detection flexibility for detecting the effects of multiple types of radiation on a sample and the effects of different samples on radiation. These four physical type measurements may be made using the same sample cell and photometer, i.e., absorbance, turbidimetric fluorescent, and nephelometric. Straylight rejection is high and the radiation intensity at each of plural wavelength groups may be measured. The liquid in the sample cell is immediately contiguous to the entrance slit for the photometer. This permits an efficient photometer system with little light loss.

BRIEF DESCRIPTION OF THE DRAWINGS

The invention may be more fully understood from the following detailed description thereof taken in connection with accompanying drawings which form a part of this application and in which:

FIG. 1 is a schematic representation of a photometer constructed in accordance with this invention;

FIG. 2 is a side elevation view of a liquid sample cell that may be used in the photometer illustrated in FIG. 1;

FIG. 3 is a cross-sectional elevation view taken along the section lines 3—3 of FIG. 2;

FIG. 4 is a cross-sectional view of the cell of FIG. 2 taken along the section line 4—4;

FIG. 6 is a plan view of a detector assembly comprising an array of photodiodes used with this invention;

FIG. 7 is a side elevation view of the detector array depicted in FIG. 6;

FIG. 11 is a pictorial view of a preferred optical measuring cell that may be used with this invention;

FIG. 12 is an end elevation view of the optical cell depicted in FIG. 11 showing the optical wall containing the exit aperture for a radiation detector;

FIG. 13 is a cross-sectional elevation view of the cell depicted in FIG. 12 taken along the section line 13—13;

DETAILED DESCRIPTION OF THE PREFERRED EMBODIMENT

Figure 5:
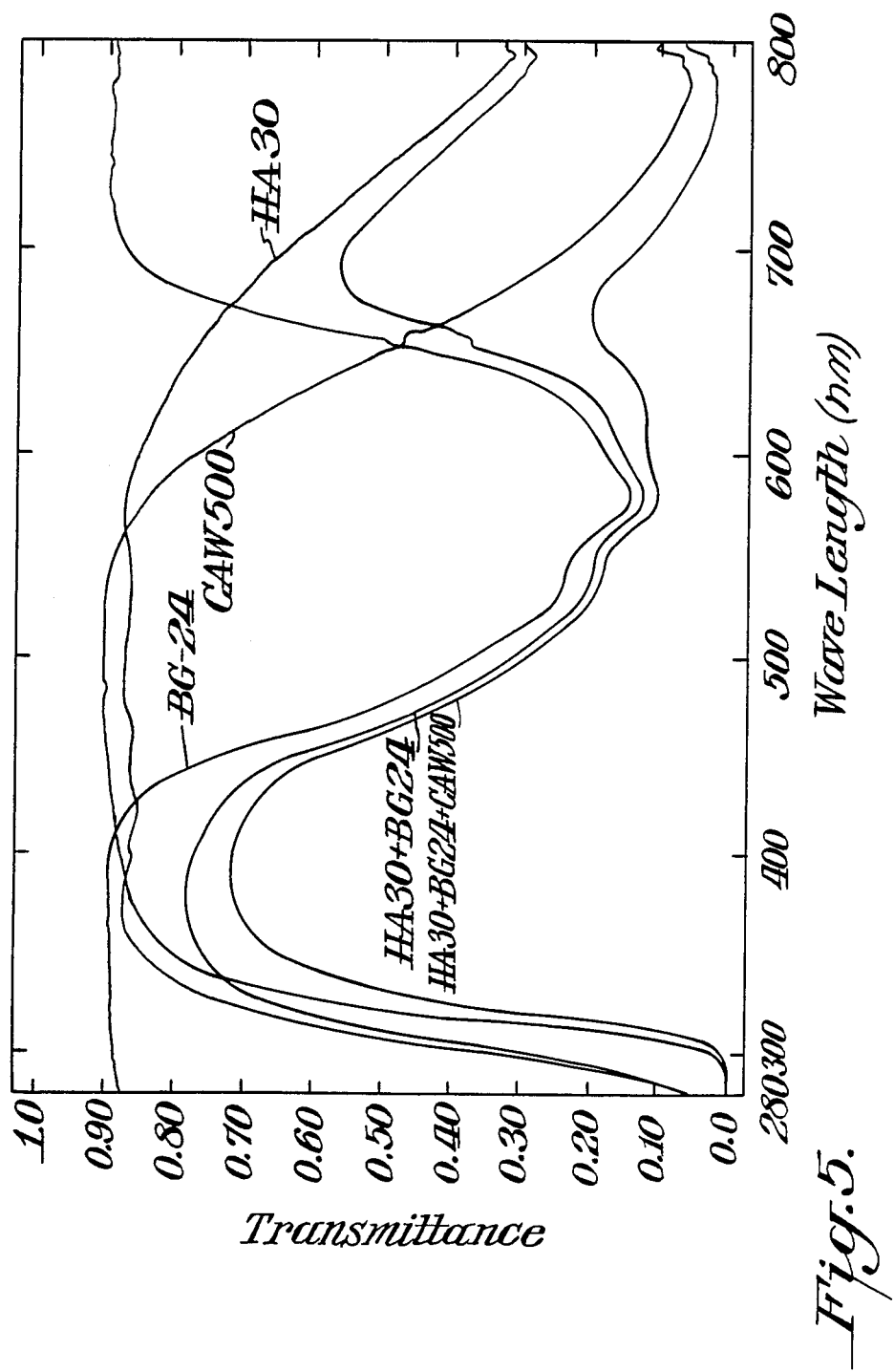
FIG. 5 is a graph of transmission versus wavelength depicting the effect of the several filters that are used to modify the sources. One set of filters modifies the tungsten lamp output so it more nearly resembles that of the xenon source used for fluorescence excitation.
Figure 8:
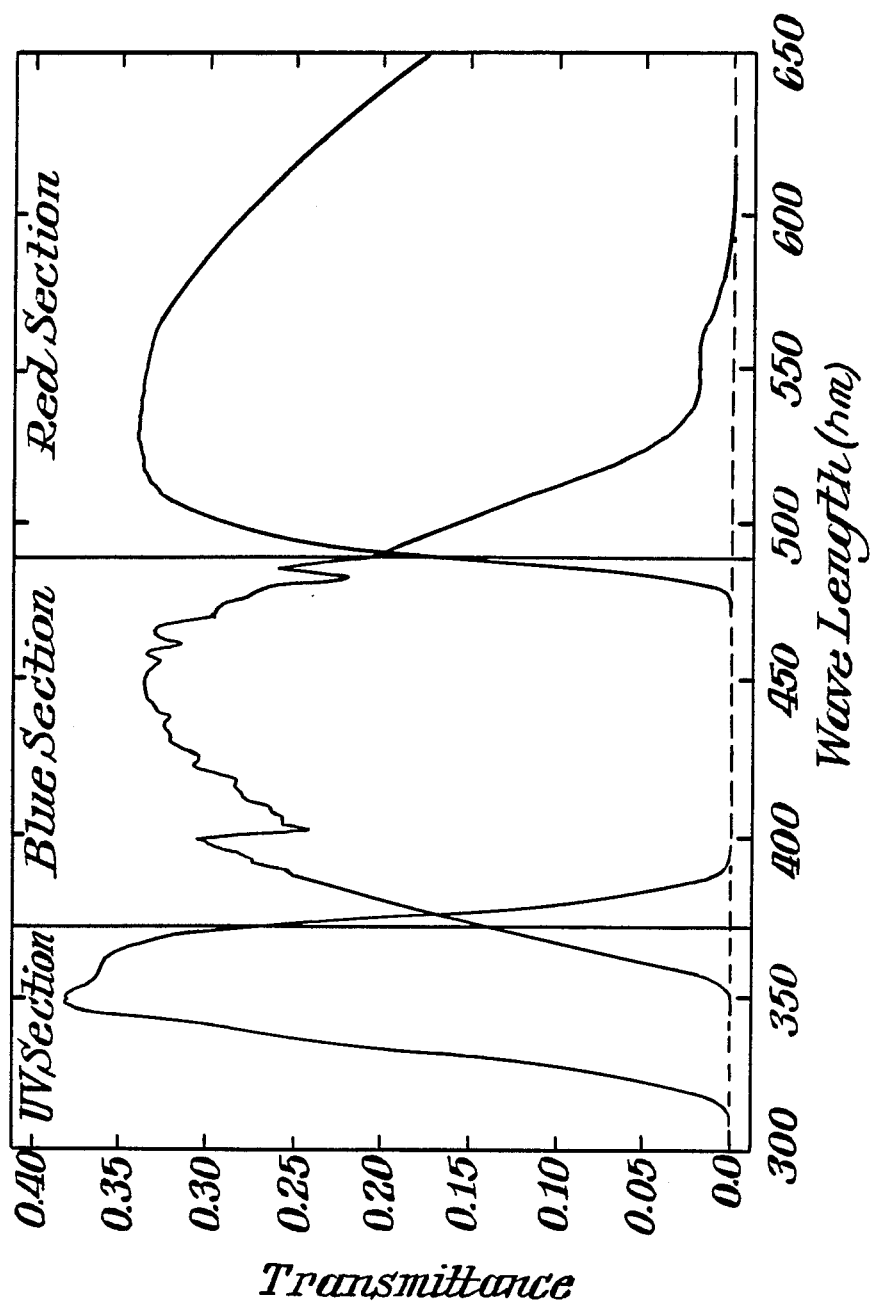
FIG. 8 is a graph of transmittance versus wavelength showing the responses of the three sections of the straylight filter used in conjunction with the array detector of FIGS. 6 and 7.

The design of a low cost photometer with combined absorbance and turbidimetric measurements on the one hand and fluorescence and nephelometric measurements on the other hand may be better understood with reference to FIGS. 1, 2, 3, and 4. It is designed to use a sample cell which may be either a batch type such as provided by a conventional cuvette or a dynamic type such as provided by a flow cell through which the liquid to be analyzed flows. The sample cell is formed to be an integral part of a grating aperture and a light or radiation source is properly positioned for wavelength dispersion of light reacting with the chemistries of the sample cell. As will be described, the grating dispersed light from the sample cell onto an array detector where the wavelength data from each detector element is the processed to provide a wavelength vs. radiation intensity relationship.

With particular reference to FIG. 1 there may be seen, for absorbance and turbidimetric measurements, a conventional continuous radiation source such as that provided by a constant tungsten halogen lamp 10. A second light radiation source 12 is also provided for fluorescence and nephelometric measurements and may be that provided by a xenon gas filled flashtube. Any other suitable sources known to those skilled in the art may be used as well. Both are placed in the optical system transverse, preferably at ninety degrees, to each other and provide the radiation necessary for these several measurements. The xenon flashtube is used for its spectral properties and high energy per pulse which enhances fluorescence and nephelometric measurements.

In order to modify the wavelength output of the tungsten source 10 to more closely match the output of the xenon flashtube terms of wavelength, a series of color glass filters are integrated into the source condenser set of lenses 14, 16. In a preferred design HA-30 and BG-24 Schott glass filters are individually optically cemented to respective plano-convex condenser lenses 14 and 16, the HA-30 glass 18 to the first lens 14 and the BG-24 filter 20 to the second lens 16.

The effect of these filters may be better understood with reference to FIG. 5. In this Figure, there are a series of curves that describe the spectral response for each filter as well as the combination. The condenser filters thus shape the tungsten lamp output to reduce the infrared energy while minimally altering the shorter wavelengths around 340 nm. This shaping is required so that the electrical capacitor selection for the amplifiers in the signal processor, as will be described hereinafter, more closely match the xenon flashtube wavelength output. With other light sources other matching filter sets will be used.

After passage through the lenses 14 and 16, light from the source 10 is passed through a shutter 22 which may be manually or automatically (by a servomotor) operated to block or pass light from the source 10. Light must be blocked from the source 10 when fluorescence measurements are to be made. Next the light from the source 10 is passed through a beam splitter 24 which may be formed of known materials for this purpose such as plate quartz. The reflected portion of the light from the source 10 is then passed through a filter 26, whose function is to filter the reflected light to a reference detector 29 to more nearly match the response characteristic of the detector for the photometer. The reference detector, which may be a photodiode of the type used in the signal processor, is used to compensate for lamp instabilities. The signal from the photodiode is processed by the signal processor as will be described.

The light which passes through the beam splitter 24 passes through a flow cell 28 which is shown more clearly in FIGS. 2 and 3. This flow cell 28 may be of a batch type in the form of a chamber housing a single cuvette in which liquid to be measured is introduced or preferably may be a dynamic flow type cell of the types shown in FIGS. 2 and 3 in which fluid is continuously flowing or stopped in the cell. The light exiting the flow cell 28 passes through a final filter 30, preferably a CAW-500 for the system described, which is cemented to the outlet wall of the flow cell as may be seen in FIG. 1. It further reduces the infrared passed by the condenser filters 18, 20 and also by the xenon source 12. The requirements for fluorescence often requires special filtering in a fluorescence excitation filter wheel which will need the additional blocking offered by the CAW-500 glass. The ultimate transmittance provided by the three filters 18, 20 and 30 (the transmittance of each being shown in FIG. 5) is depicted by the curve HA30+BG24+CAW500 in FIG. 5. It will be noted from this curve that the transmittance begins at slightly in excess of 300 nm. and is substantially inhibited at around 600 nm. with a peak pass band lying primarily between 350 and 500 nm. Other filters of course may be used depending on the desired transmission characteristics for particular applications.

The xenon source may pass through a mixing rod 34 whose function is to stabilize arc wander in the xenon source. The light from the xenon source 12 may then pass through a lens 36 and filter wheel 38 which when rotated, either manually or by a suitably stepping motor if automatic control is desired, to position various filters 40 in the optical path of the xenon source denoted by the line 42. The optical path for the light from the tungsten source is denoted by the line 44. The light passing along the xenon axis 42 then passes through a beam splitter 46 where the reflected light passes through a filter 48 whose function it is to to filter the reflected light to a reference detector and thereby reference the fluorescence/nephelometric energy input to the cell 28. This is a function similar to that described for the first reference detector 29 that provided a reference level for the signal processor. The xenon light passing through the beam splitter 46 passes through the flow cell 28 transversely or preferably perpendicularly to the axis 44 of the light from the tungsten source.

The construction of the sample cell 28 is best seen in FIGS. 2, 3 and 4. Briefly stated, the cell 28 will be seen to be formed of quartz pieces cemented together. There is an entrance piece 50, a chamber piece 52, and an exit piece 54. Each piece is in the form of a right parallelipiped internally ground or bored to define a right parallelipiped chamber 56 for the fluid to be analyzed. This provides rectangular cross-sections for the light passing along either axis 42 or 44 and hence maximizes the volume of liquid visible to the exit aperture 64. The entrance and exit pieces of quartz 50 and 54 each have inlet and exit bores leading to a taper expanding to the chamber 56 so that the fluid flowing to and from the chamber 56 has a reduced turbulence. Suitable plastic tubes 60 may be inserted through the bores 58 to provide access to the chamber 56. These tubes may be formed of a suitable inert material such as polytetrafluoroethylene (teflon). The exterior of the cell is suitably coated with an opaque material to form the entrance and exit apertures 62 and 64 (FIG. 1), respectively, for the tungsten radiation and entrance and exit apertures 66 and 68 respectively for the xenon radiation. The exit aperture 68 may be omitted and the interior cell surface mirrored if desired. Likewise the cell may be constructed of any suitable optically transparent material known to those skilled in the art.

In accordance with this invention, the exit aperture 64 has the light focused therein such that it acts as the entrance aperture for a grating 70. The grating may be a conventional reflective type holographic grating that disperses the white light or the fluorescence emission from the cell across a plurality of detector elements in an array 72 after passage through a straylight filter 74. The output of each element of the array 72 is passed to a signal processing unit 76 which samples the output from each of the elements of the array, amplifies and stores the several outputs. The output levels are compared with the reference level provided by the detectors 29 or 50 to compensate for variations in the intensity as seen at the cell entrances 62, 66.

In a preferred embodiment of the invention the array 72 has 38 detector elements and may be a silicon array supplied by Hamamatsu Plastics K.K. of Hamamatsu City, Japan. Preferably the grating is one supplied by Instruments S.A., grating number 532 02 010, which has 600 lines per mm with a spectral range approximately of 340–660 nm. over 40.6 mm. The grating is an aberration corrected holographic defraction grating that has been made by Instruments S.A. from a 90 mm diameter blank to 68 mm. If desired, the grating may be ion etched to enhance any particular region of the spectra as desired.

The straylight filter 74 (FIGS. 6 and 7) may be any conventional filter. The filter window is integrally cemented to the array element detector. The filter assists the grating by reducing scattered light in the system that would otherwise pass to the detector elements. The filter design also enhances the fluorescence detection by carefully placing the filter section lines, as may be seen in FIGS. 6 and 7, for excitation and emission cut points, matching the fluorophores that are to be used in the chemical assays. Thus as may be seen in FIGS. 6 and 7, the straylight filter is formed of three sections, a red section 78, a blue section 80 and a ultraviolet section 82. The cut line between the red and blue sections 78 and 80 may fall along the fourteenth photodiode element of the silicon array. Thus, for example, the fluoresce in excitation wavelengths fall on the blue section 80 while its emission spectra is displayed on the red section 78. The part of the filters surface closest to the array has a single layer anti-reflection coating at 340 nm. and the top surfaces has a similar coating (not shown) at 700 nm.

The 700 nm. coating is applied so that the longer wavelengths are not reflected by the top filter surface adding to system straylight rejection.

While the array detector described is preferred because of its lower cost and may be a Hamamatsu 38 element S2313 array with the straylight filter as a cover plate, it will be understood that alternative array detectors may be used. For example a Hamamatsu C2331 scanner and array may be used in place of the array and signal processing circuit 76 described.

Figure 9:
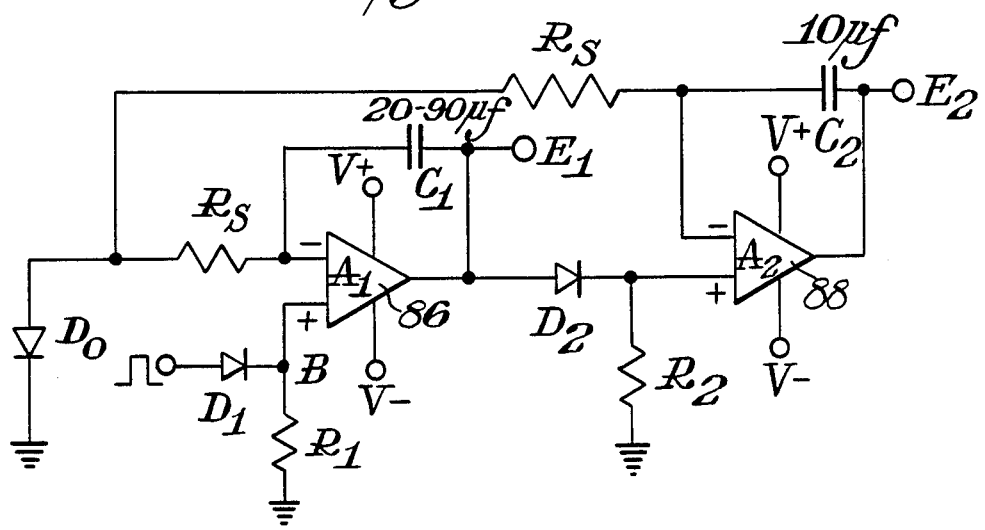
FIG. 9 is a block diagram of an integrating amplifier that may be used in conjunction with the array detector to amplify the stored signal intensities in each photodiode.
Figure 10:
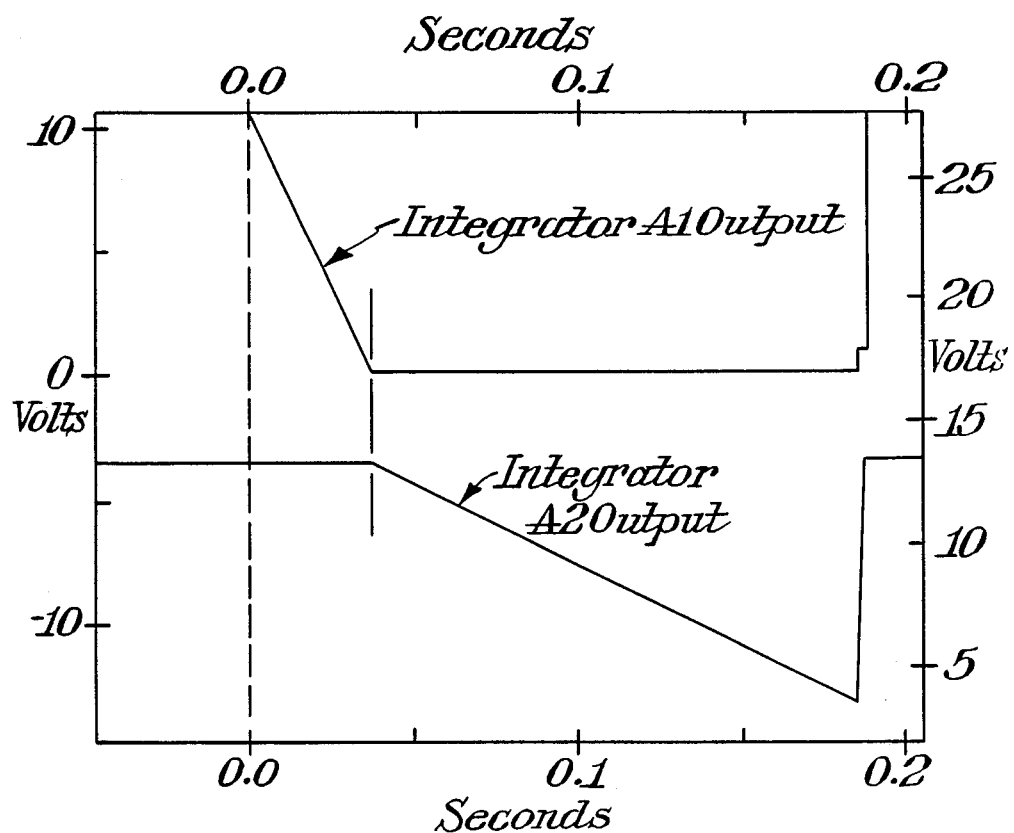
FIG. 10 is a wave form depicting the relationship of voltage versus time in the integrating amplifiers used in FIG. 9.

The details of the signal processor 76 may be best understood with reference to FIGS. 9 and 10. This signal processor consists essentially of a plurality of integrating amplifiers one for each of the photodiodes in the array detector 72. Each amplifier as seen in FIG. 9 converts the light-induced current from a photodiode DO in the array or reference detectors 29, 50 into a voltage proportional to the integral with respect to time of this photodiode current. Two serially connected integrators 86, 88 are used and they are connected in such a way that each is capable of integrating the photodiode current, but the amplifier A1 of the first integrator disables the second amplifier A2 until the first amplifier A1 saturates. After the first amplifier saturates, the second integrates the photodiode current. At any time, the total of the integration is available by measuring the output of both amplifiers and summing them after compensating for any difference in the gain of the two integrators. Except during a transition interval when the first amplifier is almost saturated and the second amplifier begins to integrate, only on amplifier is actually active at any one time.

With particular reference to FIGS. 9 and 10, DO is the silicon photodiode, one of 38 in the diode array 72 (FIGS. 6 and 7). D1 and D2 are ordinary silicon signal diodes, e.g. 1N914 or equivalent. C1 and C2 are capacitors with high insulation resistance, low dissipation factor, and low dielectric absorption, e.g. glass, polystyrene, polycarbonate, or polypropylene dielectric.

A1 and A2 are operational amplifiers with low input offset voltage and low input bias current. They also must exhibit no strange behavior (oscillations, latch-up, etc.) when the output voltage reaches the saturated limits of its range. The Texas Instruments TLC27x series CMOS integrated circuit operational amplifiers are suitable for this purpose. Many other amplifiers could also be used. Output clamping in the form of diodes returned to well regulated reference voltage supplies could be added to these other commercially available amplifiers to make them work as well.

Power for the amplifiers is labelled V+ and V−. In the circuits constructed with the TLC27x series amplifiers, V− is 0 volts (measured with respect to the grounded side of DO). The negative output saturation voltage of these amplifiers, Vsat−, includes the V− supply voltage. For other amplifiers, to obtain maximum dynamic range for A1 before A2 becomes active, it is necessary to choose V− so that Vsat− is approximately 0 volts.

In the circuits shown, V+ was chosen to give the greatest dynamic range from the analog-to-digital converter which digitized the output of A1 and A2. A value around +12 volts usually produces output voltages on some amplifiers just below +10 volts immediately after the cessation of the RESET signal. The actual output voltage under this condition is a function of the internal capacitance of DO and the capacitors C1 and C2.

The value of R2 is not critical—typically around 100 K ohms. The value of R1 is also not critical; a typical value of 1 K ohms is used because R1 and D1 are connected in common to A1 in every channel of a multi-channel amplifier for the photodiode array.

Active Mode Operation: Light impinging on DO produces a current in DO which flows out of the diode, and into C1. A1 changes its output voltage to keep the voltage difference between its inputs very close to zero—in this case the output voltage decreases due to neutralization of the charge on C1 by the current from DO. Thus the voltage at the output of A1 is equal to the voltage after the end of the reset interval, minus the integral of the photoinduced current from the photodiode, DO.

After some time this integral will equal the original voltage at the output of the amplifier, and the observed voltage will be zero. Just prior to this, the voltage appearing across R2 will be close to zero, and amplifier A2 will begin integrating the photoinduced current from DO.

During a (short) transition period, both amplifiers will be integrating the current, until amplifier A1 saturates at its negative output saturation voltage. At any time, the total integral of the photoinduced current from DO is available by measuring the change, since the end of the Reset mode, in the output voltage of both A1 and A2 and correcting for the difference in gain of the integrators as established by the capacitances of C1 and C2. From this it will be seen that the first amplifier A1 disables the second A2 until the first amplifier almost reaches negative saturation voltage. After the first amplifier saturates, the second integrates the photodiode current. At any time, the total integral is available by measuring the outputs of both amplifiers, and summing them after compensating for any difference in the gain of the two integrators. Except during the transition interval when the first amplifier is almost saturated and the second amplifier begins to integrate, only one amplifier is actually active. The outputs of these amplifiers, one for each array element and each reference detector, may be processed or recorded in the usual manner with the reference outputs subtracted logarithmically from the measured outputs to compensate for variations in source intensity. After each measurement, a reset signal is applied to the diode D1.

Reset mode operation: The non-inverting input of operational amplifier A1 is driven to a voltage more positive than the open-circuit voltage of DO plus the light induced voltage from DO plus the maximum input offset voltage for A1 (plus a safety factor). This causes the amplifier output to swing positive. The capacitor C1 couples this voltage swing to the inverting input until DO begins to conduct in the forward direction. Current flows into C1 from the output of A1 until the output voltage of A1 reaches its positive saturation voltage, Vsat+. The voltage across C1 is now Vsat+ minus V(D1).

Operational amplifier A2 and its integrating capacitor C2 will now also respond in a similar fashion to A1 and C1, because D2 couples the output of A1 to the non-inverting input of A2 to perform the same function as the RESET signal at the non-inverting input of A1.

At the end of the RESET signal, the voltage across R1 goes to 0 volts, and the output of A1 goes to a lower voltage than Vsat+. If C1 is very large compared to the internal capacitance (CO) of DO, this lower voltage will be approximately equal to the voltage across C1 described above. If C1 is equal to or smaller than C0, the new voltage at the output of A1 will be determined by the ratio of capacitances and the voltage to which each is charged during the RESET signal (C0 is charged to the voltage across D0).

In a preferred embodiment of this invention, the flow cell may be that described in copending application Ser. No. 731,780, filed May 8, 1985, entitled Optical Detector Cell by Levin et al. (IP-0579). With reference to FIGS. 11–17, the structure of the preferred optical measuring cell 110 may be seen. The cell 110 itself is constructed of various pieces of quartz, i.e., spectrocell grade, S.U.B. fused silica. In particular, the cell is configured to provide an L-shaped optical chamber 112 in which the absorbance measuring path denoted by the axis 114 lies along the horizontal leg of the L. The horizontal leg of the L is formed by four flat slab-like pieces of quartz 116 fused together in a rectangular shape to provide the horizontal leg portion of the L-shaped chamber 112. The vertical leg of the chamber 112 is formed by a second set of four pieces of quarts 118 fused together in an annulus like rectangle to define the vertical leg portion 120 of the chamber. To complete the construction of the chamber 112 an upper block of quartz 122 has a bore 129 which communicates between the vertical leg portion 120 and the exterior of the cell. To facilitate connection with tubing, a quartz tube is fused to the block 122 to communicate with the bore 129.

Alternatively the chamber 112 can be formed of three pieces of quartz, one for each of the entrance and exit faces and one for the chamber itself. In this case, the L-shaped chamber is ground into the mid portion of a solid piece of quartz and the surfaces polished.

The lower portion of the cell 110 is similarly constructed with a lower block 130 defining a bore 132 which communicates with that portion of the horizontal leg of the L-shaped chamber forming the radiation entrances of the chamber 112. Similarly, a quartz tube 134 is fused to the lower end of the block 130 at the exit region of the bore 132. A suitable chemically inert plastic tubing 136 such as tetrafluoroethylene (teflon ®) is inserted through the tubing 134 and 136 to connect liquids to the cell. the upper end 138 of the lower tubing 136 (as is also true for the lower end 129 of the upper tubing 38) has its inside diameter taperes to facilitate to the transition to the L-shaped chamber 112. Furthermore, the elements 118 forming the vertical leg portion 120 have their lower surfaces tapered upwardly at a approximately a 5° angle to facilitate the escape of air and other depris entering the cell. The upper surfaces of the elements 116 forming the horizontal leg portion are tapered similarly to complement the taper of the elements 18.

Figures 14, 15, 16, 17:
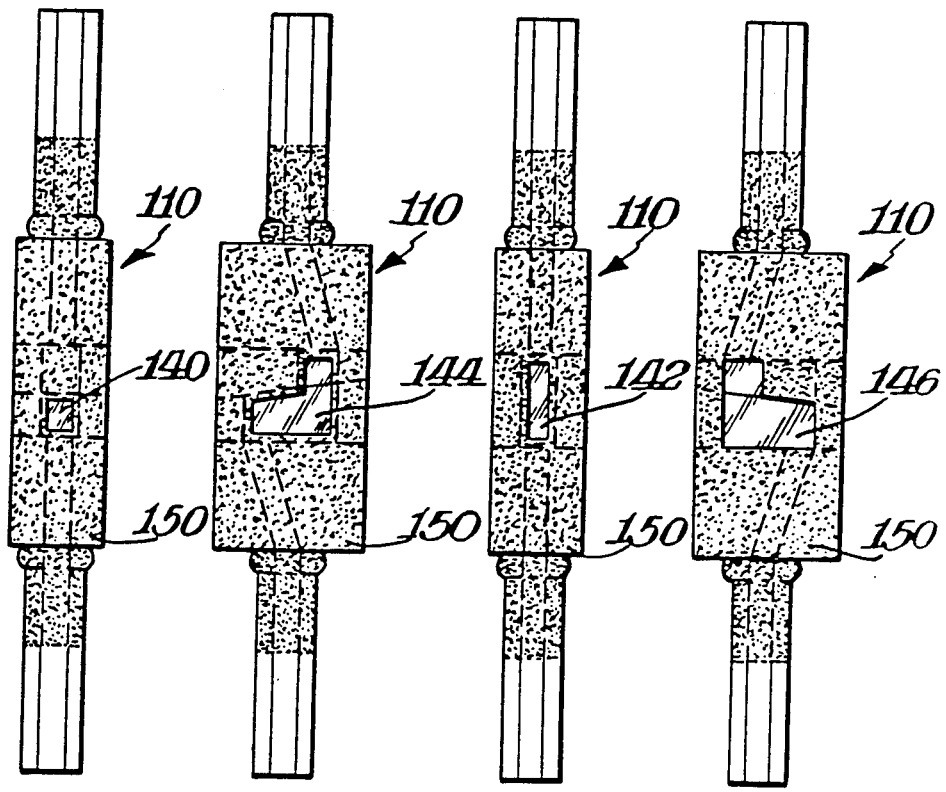
FIG. 14 is an end elevation view of the optical cell of FIG. 10 viewing the light exit aperture.
FIG. 15 is a side elevation view of the optical cell of FIG. 10 depicting the entrance aperture for the fluorescence radiation exciting source.
FIG. 16 is a side elevation view of the cell of FIG. 14 depicting the exit aperture for the fluorescence radiation exciting source.
FIG. 17 is an end back elevation view of the cell of FIG. 14 depicting the entrance aperture for the absorbance radiation.

To complete the construction of the cell, the exterior of all the elements comprising the cell are coated with, as by evaporation, chromium or similar optically opaque mirror-like material 150. This masking coating is applied to the entire exterior of the cell with the exception of those regions that provide entrance and exit windows for the absorbance and turbidimetric excitation rdiation on the one hand and for the fluorescence and nephelometric exciting source on the other hand. The fluorescence exit window may be mirrored to enhance fluorescence excitation. Thus, as may be seen in FIG. 12 a small entrance window 140 is positioned along the axis 114 to permit a source of absorbance, etc., radiation to pass along the horizontal leg of the L and through the lower half of an exit window or aperture 142 (FIG. 14). The exit aperture is narrower than the entrance window 40. For the fluorescence excitation, an L-shaped entrance window 144 is provided as seen in FIG. 15 so as to permit the entire volume of L-shaped chamber to be radiated. Similarly, a fluorescence exit window 146 as seen in FIG. 16 is provided which is slightly larger than the entrance window 144. In each case, the windows are slightly less in cross-section than the corresponding cross-section of the chamber through which the radiation is to pass. This is done to reduce the possibility of the radiation striking the walls of the chamber and creating multiple reflections therein. Finally, a shrink tubing 148 (FIG. 12) is placed over the tubing 136 and quartz tubing studs 134 to hold the tubing 136, 138 in position.

The cell thus constructed is small in internal volume and as described provides a path for the absorbance radiation along the axis 114, a path for the fluorescence excitation through the fluorescence windows 144 and 146. The liquid so excited with fluorescence radiation fluoresces and a segment of the fluorescence radiation exits through the entire exit window 142 (FIG. 13). This permits the illumination of nearly the entire volume of the cell with a corresponding portion of the fluorescence illumination passing through to the grating. In the event a full array detector is used, the exit window 142 may be sized to permit the full illumination to strike the appropriate elements. For nephelometry the illumination is through the fluorescence window 144. The resulting 90° reflections passes out through the exit window 142. Turbidity measurements are accomplished along the axis 114. As may be seen the flow channel is designed to be easily flushed and to remove all air bubbles and other material. There are few dead spaces and those that exist are a resultant of the optical needs. It should be noted that the chamber is rectangular in cross-section and has a small internal volume. The volume is only sufficient to provide the optical path lengths necessary for efficient operation of the detector.

In the operation of the photometer of this invention, in the absorbance and turbidimetric mode the shutter 22 is removed from the optical path and the constant source 10 used. A liquid sample is introduced into the cell 28. The light is focused at the entrance aperture of the cell. The sample cell and its exit aperture are an integral part of the grating aperture and absorbed or scattered light which passes through the cell is dispersed by the grating 70 and after passage through the straylight filter is detected by the array 72 and the output from each array element integrated by the signal processor 76 and passed to a suitable display instrument recorder and the like. Straylight rejection is good as has been described and sensitivity is high even though the instrument has been constructed at a relatively low cost basis.

In similar manner for fluorescence or nephelometric detection the shutter 22 is closed and the flashtube activated to pass exciting radiation to the cell 28. The material in the cell fluoresces or is refracted along the optical path 44 and out the exit aperture 64 of the cell 28 and thence to the grating for dispersion as described.

Single and bichromatic wavelength mesurements can be made and the multiwavelength analysis provided by the array 82 permits regression techniques to be used to analyze the resulting wave forms. It will be particularly noted that this photometer, although a low cost, is capable of providing absorbance, turbidimetric, fluorescence as well as nephelometric measurements all using the same flow cell.

What is claimed is:

1. In a multi-function photometer having a sample cell for containing a liquid to be measured, a grating, an array of photodiodes, and a source of radiation directed along a first axis through the cell to the grating for dispersing the radiation according to wavelength onto respective different ones of the photodiodes, thereby to provide output signals corresponding to the intensity of radiation at each wavelength, the improvement wherein the sample cell defines an exit aperture perpendicular to the first axis, the exit aperture being positioned to be the entrance aperture for the grating.

2. The photometer set forth in claim 1 wherein the sample cell has a rectangular cross-section perpendicular to the first axis that is larger in all dimensions than the exit aperture cross-section.

3. The photometer set forth in claim 2 which includes a second source of radiation directed along a second axis perpendicular to the first axis for exciting fluorescence of liquid in the sample cell, the sample cell having a fluorescent entrance aperture lying on the second axis, the fluorescent radiation exiting the cell through the grating entrance aperture.

4. The photometer set forth in claim 3 wherein the cross-sectional area of the fluorescence entrance aperture is greater than the cross-sectional area of the cell along the first axis.

5. The photometer set forth in claim 4 which includes a straylight filter disposed between the grating and the photodiode array, the filter having two filer sections, one selected to pass exciting radiation from the second source, the other selected to pass the fluorescent radiation to match that of fluorophores used in the liuqid sample.

6. The photometer set forth in claim 5 which also includes means for scanning the several output signals to obtain a wavelength related distribution of radiation intensities emitted from the sample cell.

7. The photometer set forth in claim 1 which includes a second source of radiation directed along a second axis perpendicular to the first axis for exciting fluorescence of liuqid in the sample cell, the sample cell having a fluorescent entrance aperture lying on the second axis, the fluorescent radiation exiting the cell through the grating entrance aperture.

8. The photometer set forth in claim 7 wherein the cross-sectional area of the fluorescence entrance aperture is greater than the cross-sectional area of the cell along the first axis.

9. The photometer set forth in claim 1 which includes a second source of radiation directed along a second axis perpendicular to the first axis for exciting fluorescence of liquid in the sample cell, the sample cell having a fluorescent entrance aperture lying on the second axis, the fluorescent radiation exiting the cell through the grating entrance aperture and a straylight filter disposed between the grating and photodiode array, the filter having two filter sections, one selected to pass exciting radiation from the second source, the other selected to pass the fluorescent radiation to match that of fluorophores used in the liquid sample.

10. The photometer set forth in claim 3 which includes a straylight filter disposed between the grating and the photodiode array, the filter having two filter sections, one selected to pass exciting radiation from the second source, the other selected to pass the fluorescent radiation to match that of fluorphores used in the liquid sample.

* * * * *